United States Patent
Iwamura et al.

(10) Patent No.: US 11,948,669 B2
(45) Date of Patent: Apr. 2, 2024

(54) MEDICAL INFORMATION MANAGEMENT APPARATUS AND MEDICAL INFORMATION MANAGEMENT SYSTEM

(71) Applicant: Canon Medical Systems Corporation, Otawara (JP)

(72) Inventors: Taisuke Iwamura, Utsunomiya (JP); Ichirou Maeda, Otawara (JP); Masato Shibuya, Otawara (JP); Shouichi Nogawa, Shioya (JP); Naruaki Koike, Shioya (JP)

(73) Assignee: Canon Medical Systems Corporation, Otawara (JP)

( * ) Notice: Subject to any disclaimer, the term of this patent is extended or adjusted under 35 U.S.C. 154(b) by 78 days.

(21) Appl. No.: 16/547,927

(22) Filed: Aug. 22, 2019

(65) Prior Publication Data
US 2020/0075141 A1   Mar. 5, 2020

(30) Foreign Application Priority Data

Aug. 29, 2018  (JP) .............................. 2018-160517
Aug. 2, 2019   (JP) .............................. 2019-143254

(51) Int. Cl.
| | |
|---|---|
| G16H 10/60 | (2018.01) |
| G06F 21/62 | (2013.01) |
| G16H 15/00 | (2018.01) |
| G16H 30/20 | (2018.01) |

(Continued)

(52) U.S. Cl.
CPC ......... G16H 10/60 (2018.01); G06F 21/6254 (2013.01); G16H 15/00 (2018.01);
(Continued)

(58) Field of Classification Search
CPC ........ G16H 10/60; G16H 15/00; G16H 30/20; G16H 80/00; G06F 21/6254; H04L 67/12
(Continued)

(56) References Cited

U.S. PATENT DOCUMENTS

| | | | | |
|---|---|---|---|---|
| 10,510,449 B1 * | 12/2019 | Reicher | ................ | G16H 15/00 |
| 2003/0050803 A1 * | 3/2003 | Marchosky | ............ | G16H 10/60 |
| | | | | 705/3 |

(Continued)

FOREIGN PATENT DOCUMENTS

| | | |
|---|---|---|
| JP | 2011-133958 A | 7/2011 |
| JP | 2012-221365 A | 11/2012 |

(Continued)

OTHER PUBLICATIONS

D. Wilson, D. O'Sullivan, E. McLoughlin and M. Bertolotto, "Case-Based Decision Support for Intelligent Patient Knowledge Management," 2006 3rd International IEEE Conference Intelligent Systems, London, UK, 2006, pp. 130-135, doi: 10.1109/IS.2006.348406. (Year: 2006).*

(Continued)

*Primary Examiner* — Christopher L Gilligan
*Assistant Examiner* — Bennett Stephen Erickson
(74) *Attorney, Agent, or Firm* — Oblon, McClelland, Maier & Neustadt, L.L.P.

(57) ABSTRACT

A medical information management apparatus has processing circuitry configured to search medical information in a storage, when accepting a search request of the medical information including a key being an item of information regarding a patient and a value being contents of the key, and extract the medical information matching a search condition as condition-matched medical information; extract the key and the value from the condition-matched medical information, calculate a matching rate being a proportion of the value included in the condition-matched medical information to the entire medical information in the storage, and determine that the value is idiosyncratic information when the matching rate is equal to or less than a threshold set with respect to the key; and determine whether the key of the (Continued)

value determined to include the idiosyncratic information corresponds to an essential key which is essential in terms of a purpose of utilization.

20 Claims, 8 Drawing Sheets

(51) Int. Cl.
*G16H 80/00* (2018.01)
*H04L 67/12* (2022.01)

(52) U.S. Cl.
CPC ............. *G16H 30/20* (2018.01); *G16H 80/00* (2018.01); *H04L 67/12* (2013.01)

(58) Field of Classification Search
USPC ........................................................... 705/2
See application file for complete search history.

(56) References Cited

U.S. PATENT DOCUMENTS

| 2007/0106754 | A1* | 5/2007 | Moore | ................... G16H 40/20 707/E17.116 |
| 2010/0042583 | A1* | 2/2010 | Gervais | ............... G06F 21/6254 707/757 |
| 2013/0290826 | A1 | 10/2013 | Niwa et al. | |
| 2014/0379528 | A1* | 12/2014 | Martin | ............... G06Q 30/0641 705/26.62 |
| 2019/0311810 | A1* | 10/2019 | Sevenster | .............. G06N 5/022 |
| 2020/0286632 | A1* | 9/2020 | Takahata | ............. G06F 21/6245 |
| 2020/0350072 | A1* | 11/2020 | McEwing | .............. G16H 50/70 |

FOREIGN PATENT DOCUMENTS

| JP | 2013-132514 A | 7/2013 |
| JP | 2014-153943 A | 8/2014 |
| JP | 2015-160085 A | 9/2015 |
| JP | 2016-048530 A | 4/2016 |
| JP | 2017-073022 A | 4/2017 |
| JP | 2017-097654 A | 6/2017 |

OTHER PUBLICATIONS

Japanese Office Action dated Aug. 4, 2023 in Japanese Patent Application No. 2019-143254 (with English translation), 5 pages.

* cited by examiner

| KEY | THRESHOLD |
|---|---|
| ESTABLISHED NAME OF DISEASE | 0.01% |
| ALLERGY INFORMATION | 0.1% |
| NUMBER OF DAYS IN HOSPITAL | 1% |
|  |  |
| . . . | . . . |

FIG. 6

| PURPOSE OF UTILIZATION | ESSENTIAL KEY |
|---|---|
| RESEARCH: LUNG CANCER | GENDER, AGE, BMI, BIOMARKER |
|  |  |
| . . . | . . . |

FIG. 7

|  |  | KEY | | | |
|---|---|---|---|---|---|
|  |  | GENDER | AGE | NUMBER OF DAYS IN HOSPITAL | MODALITY | ... |
| RESEARCH |  |  |  |  |  |  |
|  | LUNG CANCER | ■ | ■ | □ | □ | ... |
|  | ... |  |  |  |  |  |
| CONFERENCE PRESENTATION |  |  |  |  |  |  |
|  | ... |  |  |  |  |  |

FIG. 8

| AGE | GENDER | NUMBER OF DAYS IN HOSPITAL | ... | RESULT | ANONYMIZATION |
|---|---|---|---|---|---|
| 45 | M | 3 |  | OK |  |
| 50 | F | 20 |  | OK |  |
| 49 | M | 4 |  | OK |  |
| 102 (ESSENTIAL KEY) | M | 5 |  | NG | [EXECUTION] ~ B2 |
| 51 | F | 7 |  | OK |  |
| 42 | M | 5 |  | OK |  |

FIG. 9

| RESEARCHER | | | | | |
|---|---|---|---|---|---|
| | HEPATIC DISEASE | | | | |
| | | HEPATITIS | | | |
| | | | HEPATIC FEVER | | |
| | | | CHRONIC HEPATITIS | | |
| | | | FULMINANT HEPATITIS | | |
| | | | | | |
| | | | | | |
| | | | | | |
| | | | | | |
| | | | | | |

MEDICAL INFORMATION MANAGEMENT APPARATUS AND MEDICAL INFORMATION MANAGEMENT SYSTEM

CROSS-REFERENCE TO RELATED APPLICATIONS

This application is based upon and claims the benefit of priority from Japanese Patent Applications No. 2018-160517, filed on Aug. 29, 2018 and No. 2019-143254, filed on Aug. 2, 2019; the entire contents of which are incorporated herein by reference.

FIELD

Embodiments of the present invention relate to a medical information management apparatus and a medical information management system.

BACKGROUND

In recent medical sites, for example, a medical image such as an X-ray image or a CT (Computed Tomography) image is replaced with digital image data, and managed by a medical image management system. Personal information such as a full name, an address, and a telephone number of a relevant patient and disease information such as an established name of disease and allergy information are managed as medical information by the medical information management system. The medical information managed by the medical information management system and the medical image managed by the medical image management system are managed by being linked by a patient ID or the like being unique identification information which identifies patients.

It is needless to say that these pieces of medical information managed by the medical information management system are utilized by a clinician when he/she examines a patient, and other than the above, these pieces of medical information are sometimes utilized by a user such as a researcher for the purpose of academic research and the like. Regarding such secondary usage of the medical information, there is a need to perform anonymization processing from a viewpoint of protection of personal information. Regarding the anonymization, a guide is indicated in a guideline and the like, and it is also proposed to perform processing by using an anonymization template (Patent Document 1).

However, by the amendment of Personal Information Protection Law in 2017, there is indicated a guide of "deleting an idiosyncratic description and the like (a description which may constitute a description and the like capable of identifying a specific individual because of its idiosyncrasy) when creating anonymously processed information". Idiosyncratic information being the idiosyncratic description and the like is difficult to be deleted by conventional anonymization processing, so that when performing the anonymization, a user such as a researcher has to make judgment manually.

BRIEF DESCRIPTION OF THE DRAWINGS

FIG. 5 is a diagram illustrating one example of a search request screen which is displayed on a terminal of a user being a researcher and the like;

FIG. 8 is a diagram illustrating one example of an essential key setting screen which is displayed on a terminal of a user being a researcher and the like;

FIG. 9 is a diagram illustrating one example of a confirmation screen which is displayed on a terminal of a user being a researcher and the like;

FIG. 10 is a diagram illustrating one example of a rounding setting screen which is displayed on a terminal of a user being a researcher and the like;

DETAILED DESCRIPTION

Hereinafter, a medical information management system according to embodiments will be described while referring to the drawings. Note that components having substantially the same functions and configurations will be denoted by the same numerals and duplicated explanation will be made only in a necessary case in the following explanation.

First Embodiment

Figure 1:
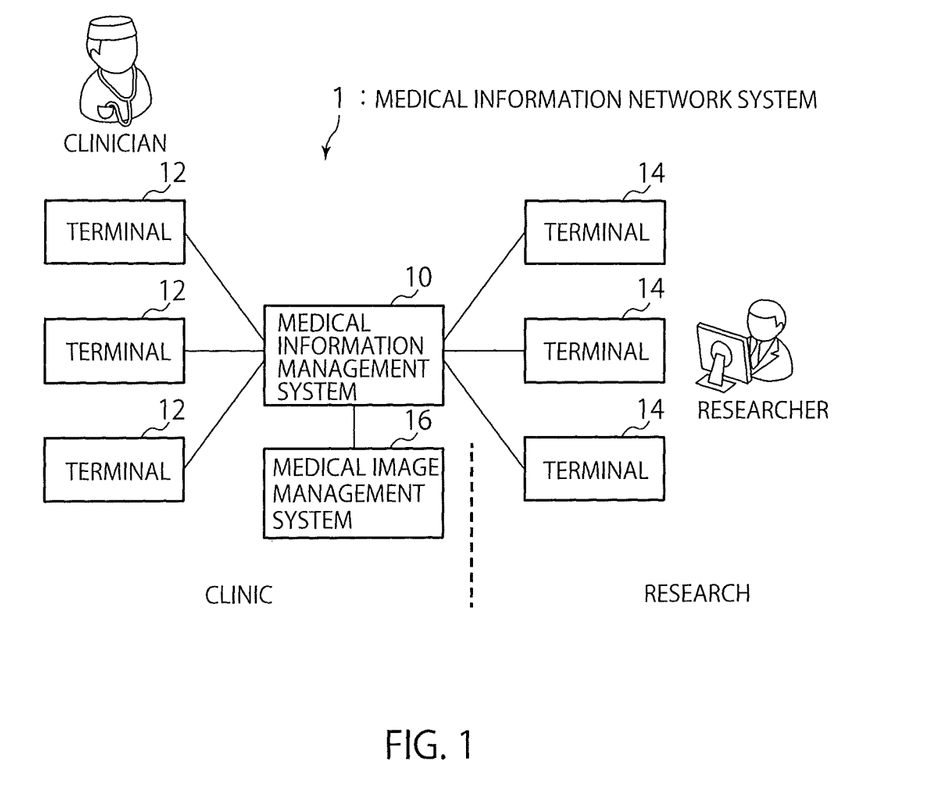
FIG. 1 is a block diagram explaining the entire configuration of a medical information network system according to a first embodiment.

FIG. 1 is a block diagram explaining the entire configuration of a medical information network system 1 according to a first embodiment. As illustrated in FIG. 1, the medical information network system 1 according to the present embodiment is configured by including a medical information management system 10 which manages medical information of a hospital and the like where it is installed, one or plural terminals 12 used by a user such as a clinician, and one or plural terminals 14 used by a user such as a researcher. In addition, the medical information network system 1 according to the present embodiment is configured by including a medical image management system 16.

The medical information management system 10 manages, for example, personal information which specifies an individual patient such as a full name, an address, and a telephone number of a patient, and disease information such as an established name of disease and allergy information of the patient. The personal information and the disease information managed by the medical information management system 10 are linked to a medical image such as an X-ray image or a CT image of the patient managed by the medical image management system 16. For example, each of the medical information management system 10 and the medical image management system 16 can be configured by a computer which is a so-called server having a high processing capability.

The terminal 12 is connected to the medical information management system 10 via a network, and a user such as a clinician can refer to medical information of a patient, newly add medical information, and edit the existing medical information when he/she examines the patient. For example, the terminal 12 can be configured by a computer which is a so-called personal computer having not so high processing capability.

The terminal 14 is also connected to the medical information management system 10 via the network, and a user such as a researcher can refer to or obtain medical information accumulated in the medical information management system 10 to secondarily utilize the medical information when he/she researches cases and the like. For example, the terminal 14 can also be configured by a computer which is a so-called personal computer having not so high processing capability.

Figure 2:
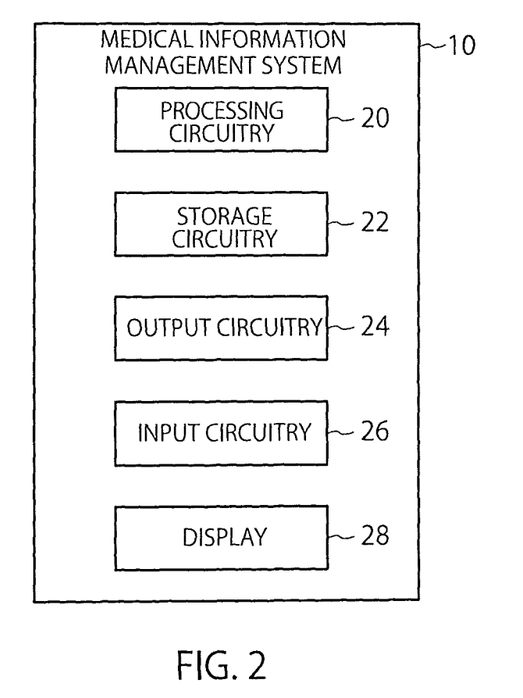
FIG. 2 is a block diagram explaining one example of an internal configuration of a medical information management system according to the first embodiment.

FIG. 2 is a block diagram explaining one example of an internal configuration of the medical information management system 10 in FIG. 1. As illustrated in FIG. 2, the medical information management system 10 according to the present embodiment is configured by including processing circuitry 20, storage circuitry 22, output circuitry 24, input circuitry 26, and a display 28.

The processing circuitry 20 is a processing unit which performs various kinds of processing such as anonymization processing of medical information, and it can be configured by a processor, a memory, or the like, for example. The word processor here means, for example, a CPU (Central Processing Unit), a GPU (Graphics Processing Unit), or circuitry such as an application specific integrated circuitry (ASIC), or a programmable logic device (for example, a simple programmable logic device: SPLD), a complex programmable logic device (CPLD), and a field programmable gate array (FPGA)). The processor realizes the functions by reading and executing the programs stored in the storage circuitry 22. Note that instead of storing the programs in the storage circuitry 22, the programs may be configured to be directly installed in circuitry of the processor. In this case, the processor reads and executes the programs installed in the circuitry, to thereby realize the functions. Note that the processor is not limited to the case of being configured as a single processor circuitry, but a plurality of independent circuitry may be combined together to constitute one processor to realize the functions. Further, the plurality of components in FIG. 2 may be integrated into one processor to realize the functions.

The storage circuitry 22 is circuitry which stores and holds medical information of a patient, and it can be configured by, for example, a hard disk drive (HDD), a solid state drive (SSD), or the like. Further, the storage circuitry 22 temporarily or permanently stores various kinds of data which are generated when the processing circuitry 20 executes various kinds of processing. The medical information includes personal information such as a full name, an address, and a telephone number of a patient, disease information such as an established name of disease and allergy information, and information such as a nurse's record and an electronic medical chart. This storage circuitry 22 may be configured by one piece of hardware or plural pieces of hardware. When the storage circuitry 22 is configured by plural pieces of hardware, it may also be configured by a combination of different kinds of hardware such as a hard disk drive and a solid state drive.

The output circuitry 24 is circuitry which outputs medical information of a patient in accordance with a search request issued by the terminal 12 or the terminal 14. For example, the output circuitry 24 obtains medical information of a patient which matches a search condition from the storage circuitry 22, and outputs the medical information to the terminal 12 or the terminal 14 via the network. The terminal 12 or the terminal 14 displays the medical information output from the output circuitry 24 on a display and the like to allow a user such as a clinician or a researcher to browse the medical information.

The input circuitry 26 is circuitry which accepts various kinds of inputs from the terminal 12 or the terminal 14, and in the present embodiment, in particular, a user inputs a request or information required for anonymizing the medical information. Concretely, a request or information input by the user through the operation of the terminal 12 or the terminal 14 is input into the input circuitry 26 via the network. Based on the request or the information input into the input circuitry 26, the processing circuitry 20 executes various kinds of processing, stores the information in the storage circuitry 22, and reads the information from the storage circuitry 22.

Further, the input circuitry 26 is also circuitry which directly inputs a request or information into the medical information management system 10, and in this case, the input circuitry 26 can be configured by, for example, a keyboard, a mouse, a touch panel, or the like connected to the medical information management system 10. For example, a manager who manages the medical information management system 10 inputs a necessary request or information into the medical information management system 10 via the input circuitry 26.

The display 28 is a device which displays various kinds of information including the medical information, and it can be configured by, for example, a liquid crystal display, a CRT (Cathode Ray Tube), or the like. For example, in the present embodiment, a manager of the medical information management system 10 inputs a request which is necessary for managing the medical information management system 10 through the input circuitry 26, and makes a result thereof to be displayed on the display 28.

Figure 3:
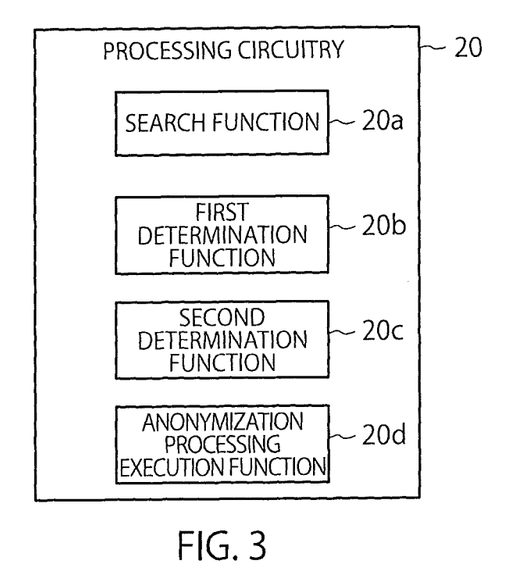
FIG. 3 is a diagram representing, by functional blocks, processing circuitry in the medical information management system according to the first embodiment.

FIG. 3 is a diagram representing, by functional blocks, the processing circuitry 20 in the medical information management system 10 according to the present embodiment. As illustrated in FIG. 3, the processing circuitry 20 according to the present embodiment configures a search function 20a, a first determination function 20b, a second determination function 20c, and an anonymization processing execution function 20d. Concretely, the processing circuitry 20 reads and executes various kinds of programs stored in the storage circuitry 22, to thereby realize these search function 20a, first determination function 20b, second determination function 20c, and anonymization processing execution function 20d. In the present embodiment, the search function 20a configures a searcher, the first determination function 20b configures a first determiner, the second determination function 20c configures a second determiner, and the anonymization processing execution function 20d configures an anonymization processing executor. Further, a medical information management apparatus in the present embodiment is configured by the processing circuitry including the search function 20a, the first determination function 20b, the second determination function 20c, and the anonymization processing execution function 20d.

Figure 4:
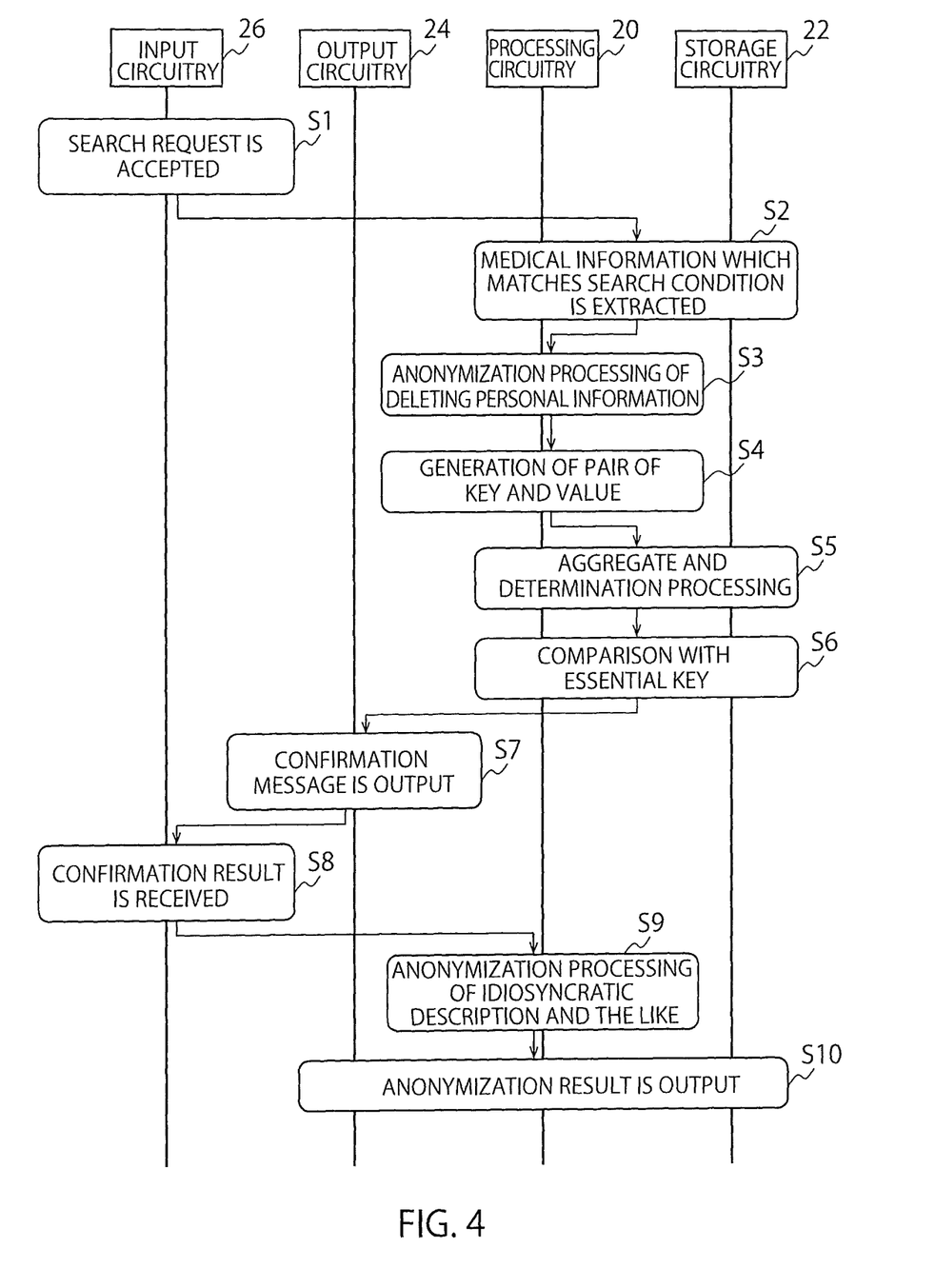
FIG. 4 is a diagram illustrating a processing flow which explains contents of anonymization processing executed by the medical information management system according to the first embodiment.

FIG. 4 is a diagram illustrating a processing flow which explains contents of anonymization processing executed by the medical information management system 10 according to the present embodiment. As illustrated in FIG. 4, the medical information management system 10 accepts a search request of the medical information (step S1). Concretely, the input circuitry 26 of the medical information management system 10 first accepts a search request from the terminal 14 of a user such as a researcher.

Figure 5:
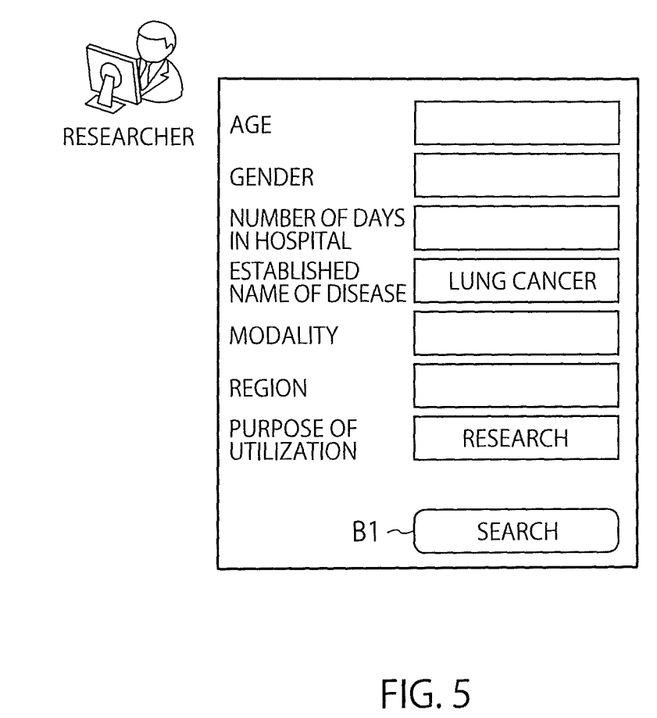

FIG. 5 is a diagram illustrating one example of a search request screen which is displayed on the terminal 14 according to the present embodiment. As illustrated in FIG. 5, the user such as the researcher first inputs information which specifies a search condition into the terminal 14. On the search request screen in FIG. 5, for example, age, gender, the number of days in the hospital, an established name of disease, modality, a region, and a purpose of utilization are prepared on the left side region of the search request screen as input items for setting the search condition. Further, the example of FIG. 5 illustrates a state where the user inputs "lung cancer" as the established name of disease, and inputs "research" as the purpose of utilization.

When, in this state, the user clicks a search button B1, the search request is generated, and transmitted to the medical information management system 10 via the network. This search request is input into the input circuitry 26, and the search function 20a in the processing circuitry 20 extracts the medical information which matches the search condition from the storage circuitry 22 (step S2). Hereinbelow, this extracted medical information is set to condition-matched medical information. Note that it is also possible to design such that the search function 20a in the processing circuitry 20 also extracts, based on a designation and the like from the user, a medical image such as an X-ray image or a CT image of a patient linked to the medical information which matches the search condition from the medical image management system 16 as the condition-matched medical information.

Next, as illustrated in FIG. 4, the anonymization processing execution function 20d in the processing circuitry 20 of the medical information management system 10 performs anonymization processing of deleting personal information from the extracted condition-matched medical information (step S3). In the anonymization processing of deleting the personal information, for example, the anonymization processing execution function 20d in the processing circuitry 20 deletes the full name, the address, the telephone number, and so on. Note that when the medical image such as the X-ray image or the CT image of the patient is also extracted as the condition-matched medical information, and the medical image includes information which specifies the individual such as the full name (tag information), the anonymization processing execution function 20d deletes this information as well.

Next, the first determination function 20b in the processing circuitry 20 of the medical information management system 10 generates a pair of a key and a value from the condition-matched medical information after being subjected to the processing in step S3 (step S4). Here, the key is an item of information regarding a patient such as an established name of disease, allergy information, and the number of days in the hospital, and is information to be a key for search or narrowing. Meanwhile, the value is contents of the key. For example, the items such as the age, the gender, the established name of disease, the number of days in the hospital, and the modality in the medical information are the keys. Further, for example, when the established name of disease is set to the key, the values of the key are lung cancer, liver cancer, and hepatic fever. As described above, in the present embodiment, the medical information is configured by including at least one or plural keys and the value being the contents of the key.

Further, in the present embodiment, when the key is composed of a sentence such as an observation, it is possible to extract a keyword included in the sentence and set the keyword as the value. In this case, the number of the keyword may be not one but plural, and plural values are set with respect to one key.

Next, as illustrated in FIG. 4, the first determination function 20b in the processing circuitry 20 of the medical information management system 10 performs an aggregate with respect to the medical information stored in the storage circuitry 22, by using the key extracted in step S4, and calculates a matching rate of the value extracted in step S4 (step S5). Namely, a matching rate being a proportion of each key included in the condition-matched medical information to the entire medical information stored in the storage circuitry 22 is calculated and extracted in step S4. For example, an aggregate is performed regarding the key of the established name of disease, and calculation regarding how much is a proportion occupied by lung cancer in the total number of cases of the medical information of patients storing the established names of diseases, is performed. Similarly, a matching rate of a value of another key included in the condition-matched medical information is also calculated in a similar manner. Subsequently, when this matching rate is equal to or less than a predetermined threshold set for each key, the first determination function 20b in the processing circuitry 20 determines that the value is idiosyncratic information being an idiosyncratic description and the like.

Figure 6:
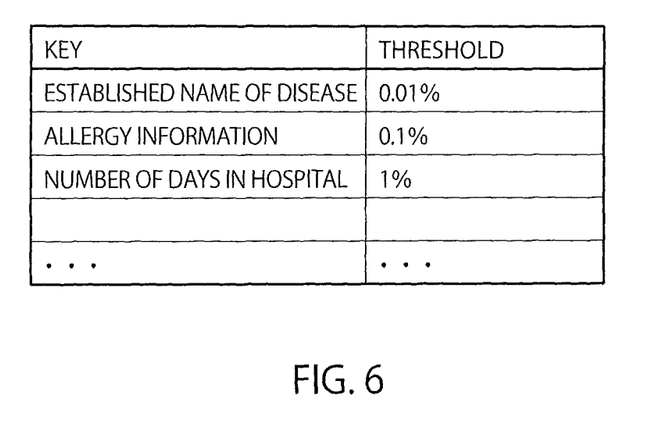
FIG. 6 is a diagram illustrating one example of a threshold table holding a relationship between a key and a threshold.

FIG. 6 is a diagram illustrating one example of a threshold table holding a relationship between a key and a threshold. In the present embodiment, this threshold table is stored and held in the storage circuitry 22, for example, and it is appropriately read to be utilized by the processing circuitry 20. This example of the threshold table in FIG. 6 indicates that a threshold of the established name of disease is 0.01%, a threshold of the allergy information is 0.1%, and a threshold of the number of days in the hospital is 1%. Specifically, it is indicated that in a case where the established name of disease is the key, there is a high possibility that a patient is specified when a matching rate of the value is 0.01% or less, and in a case where the allergy information is the key, there is a high possibility that a patient is specified when a matching rate of the value is 0.1% or less. For this reason, in the example of the search request generated in FIG. 5, the key is the established name of disease, and the value is the lung cancer, so that when the matching rate of the lung cancer with respect to the entire medical information is 0.01% or less, it is determined that the established name of disease is an idiosyncratic description and the like.

When calculating the matching rate, it is also possible to calculate the matching rate based on not only a perfectly-matched value but also synonyms which are regarded to be matched with the value. For example, when the key is the established name of disease and the value is cancer, it is also possible to calculate the matching rate based on not only the cancer but also synonyms such as a malignant tumor and a neoplasm which are regarded to be matched with the cancer.

Further, the threshold of the matching rate may also employ a fixed value without using the threshold table as in FIG. 6. In this case, it is also possible to design such that a fixed value is set as the medical information management system 10, or an original fixed value can be set in the medical information management system 10 for each hospital facility.

Further, when the key is composed of a sentence such as an observation, it can also be considered a case where plural values are set with respect to one key. In such a case, it is also possible to perform not only calculation of a matching rate based on an individual value but also calculation of a matching rate based on a combination of the plural values. For example, when the key is the observation, and the values are lung cancer and hypertension, a matching rate of the lung cancer and a matching rate of the hypertension may be calculated individually, or a matching rate of the lung cancer and the hypertension may be calculated in addition to this.

Next, as illustrated in FIG. 4, the second determination function 20c in the processing circuitry 20 of the medical information management system 10 compares the key determined as the idiosyncratic information and an essential key linked to the purpose of utilization (step S6). Here, the essential key means an item such that, in view of the purpose of utilization, if information of that key cannot be obtained, the purpose of utilization cannot be achieved as the medical information. Subsequently, the second determination function 20c in the processing circuitry 20 generates a determination result indicating whether or not the key determined as the idiosyncratic information corresponds to the essential key linked to the purpose of utilization.

Figure 7:
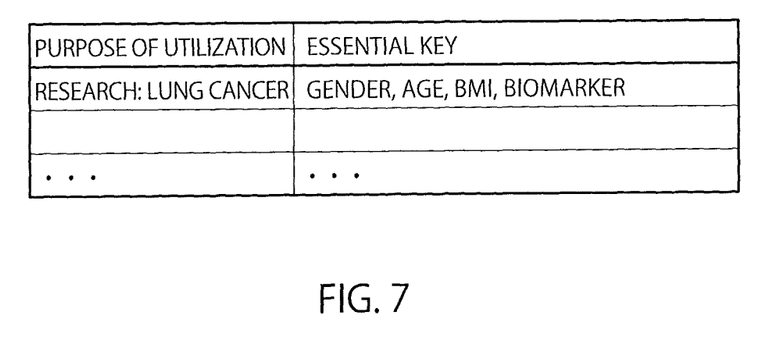
FIG. 7 is a diagram illustrating one example of an essential key table holding a correspondence between a purpose of utilization and an essential key.

FIG. 7 is a diagram illustrating one example of an essential key table holding a correspondence between the purpose of utilization and the essential key. In the present embodiment, this essential key table is stored and held in the storage circuitry 22, for example, and it is appropriately read to be utilized by the processing circuitry 20. This example of the essential key table in FIG. 7 indicates that when the purpose of utilization is research and a search target is lung cancer being the established name of disease, gender, age, BMI (Body Mass Index), and a biomarker are essential keys.

Figure 8:
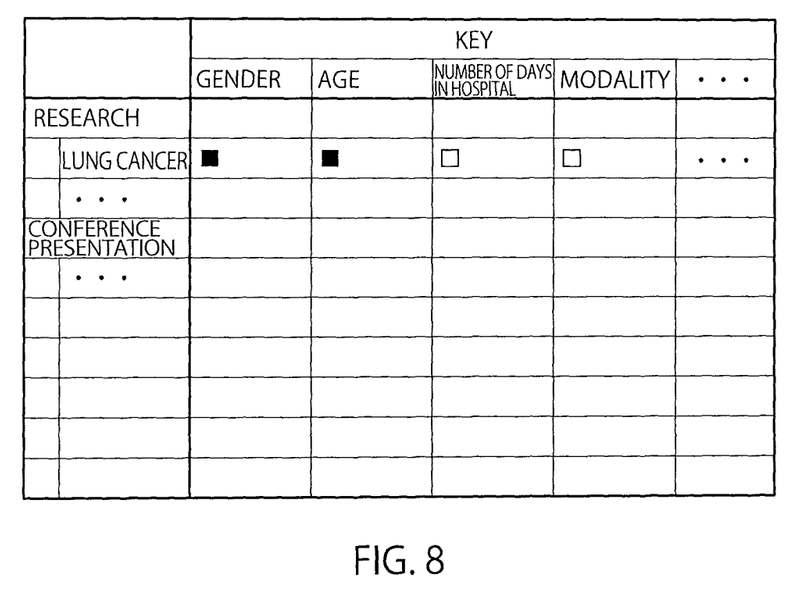

This essential key table in FIG. 7 may be previously set and stored in the storage circuitry 22, or it is also possible to design such that a user can change the setting according to need. FIG. 8 is a diagram illustrating one example of an essential key setting screen which is displayed on the terminal 14 in order to allow a user of the terminal 14 to arbitrarily set the essential key. As illustrated in FIG. 8, the user of the terminal 14 makes the essential key setting screen to be displayed, and clicks to select a key which he/she considers as the essential key. In the example of FIG. 8, a quadrangle colored in black indicates a state of being selected as the essential key, and a quadrangle colored in white indicates a state of not being selected as the essential key. It is configured such that when the user clicks the quadrangular portion, the portion colored in black indicating the selected state and the portion colored in white indicating the unselected state are alternately switched. Here, a state is exemplified in which the gender and the age are set as the essential keys when the purpose of utilization for the user is research of lung cancer. By transmitting this setting to the medical information management system 10 from the terminal 14, the essential key table stored in the storage circuitry 22 is updated. However, the purpose of utilization does not always have to be defined in a manner that contents of utilization action such as research or conference presentation and the established name of disease are prepared as a set, and the purpose of utilization can be defined in various forms.

Note that the setting of the essential key table as above may also be performed by a manager of the medical information management system 10. In this case, the essential key setting screen in FIG. 8 is displayed on the display 28 in FIG. 2, and the manager of the medical information management system 10 operates the displayed essential key setting screen to change the setting of the essential key table stored in the storage circuitry 22.

Figure 9:
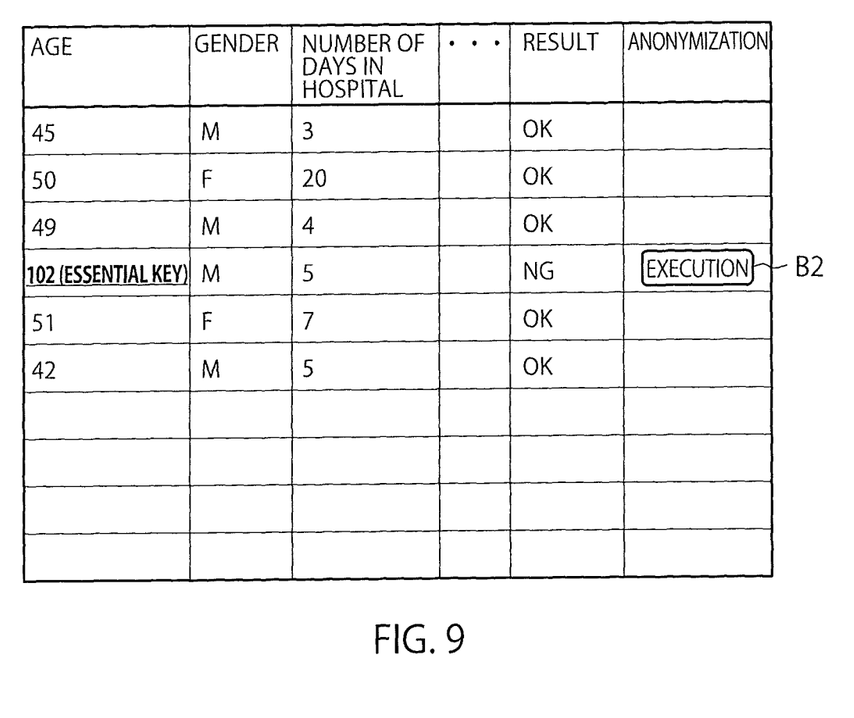

Next, as illustrated in FIG. 4, the processing circuitry 20 of the medical information management system 10 outputs to transmit a confirmation message to the terminal 14 of the user such as the researcher via the output circuitry 24 (step S7). The terminal 14 of the user such as the researcher receiving this confirmation message displays, on its screen, a confirmation screen such as illustrated in FIG. 9, for example. Specifically, the message transmitted to the terminal 14 from the medical information management system 10 includes at least the extracted condition-matched medical information including the age, the gender, the number of days in the hospital, and so on, the determination result indicating whether or not the idiosyncratic information exists in the extracted condition-matched medical information, and the determination result indicating whether or not the key of the value in which the idiosyncratic information exists is set as the essential key. For this reason, the terminal 14 receiving the confirmation message generates the confirmation screen based on the condition-matched medical information of a patient, and displays, on the confirmation screen, the determination result indicating whether or not the idiosyncratic information being the idiosyncratic description and the like exists and the determination result indicating whether or not the key including the idiosyncratic information corresponds to the essential key.

In the example of FIG. 9, items of keys such as the age, the gender, and the number of days in the hospital are displayed on a first line on the confirmation screen. Further, on a second line and lines thereafter on the confirmation screen, values with respect to the respective keys are displayed.

Besides, on the confirmation screen, the determination result indicating whether or not the idiosyncratic information exists in the extracted condition-matched medical information is displayed. Specifically, information indicating that the determination result is NG, is displayed with respect to information of a patient in which it is determined that the idiosyncratic information exists in the extracted key in step S5 in FIG. 4. On the contrary, information indicating that the determination result is OK, is displayed with respect to information of a patient in which it is determined that the idiosyncratic information does not exist in the extracted key in step S5 in FIG. 4. In the example of FIG. 9, the determination result of a fourth patient from the top is NG, and determination results of the other patients are OK. Further, when the determination result is NG, a display is made in a manner that the user such as the researcher can understand that the determination result becomes NG because of which key. In the example of FIG. 9, the value of the key being equal to or less than the threshold in step S5 in FIG. 4 is represented by underlined bold characters. In the example of FIG. 9, it can be understood that the determination result becomes NG because the age of the fourth patient from the top is 102. Besides, since the age is the essential key in view of the purpose of utilization of the research of lung cancer, a display indicating that the key is the essential key is made on a side of the value being the age of 102.

When, on the confirmation screen displayed as above, the user such as the researcher judges that anonymization of the fourth patient from the top is allowed to be performed, the user clicks an anonymization execution button B2 which exists on a column of anonymization. Meanwhile, the key being the age is the essential key when the purpose of utilization is the research of lung cancer. For this reason, if the information of the age of 102 is lost, the meaning of obtaining the medical information may be eliminated in the first place. In such a case, the user such as the researcher does not click the anonymization execution button B2 and gives up the obtainment of the medical information.

Figure 10:
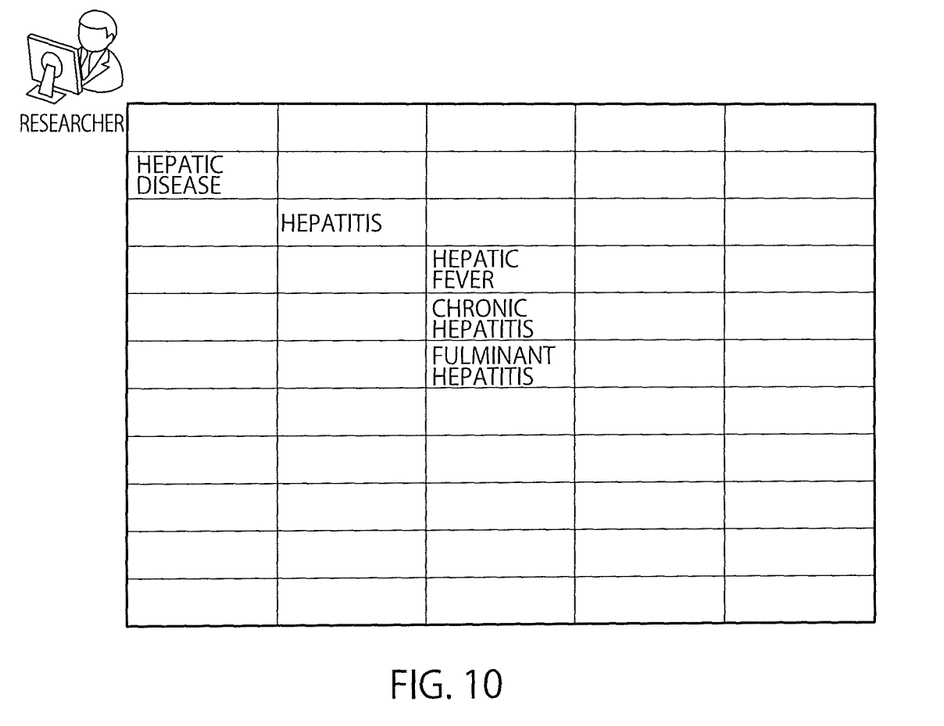

For this reason, in the medical information management system 10 according to the present embodiment, the method of anonymization employs not only the deletion but also a method of rounding. FIG. 10 is a diagram illustrating one example of a rounding setting screen. This rounding setting screen is displayed on the terminal 14 of the user such as the researcher, separately from the confirmation screen in FIG. 9. The rounding setting screen in FIG. 10 exemplifies a rounding setting screen of established names of diseases relating to hepatitis.

As illustrated in FIG. 10, hepatic disease being the established name of disease is a name of disease of the broadest concept, and as the established name of disease of a subordinate concept thereof, there exists hepatitis. As a subordinate concept of hepatitis, there exist hepatic fever, chronic hepatitis, and fulminant hepatitis. In such a case, for example, when the user such as the researcher sets hepatic fever as the established name of disease to the search condition, by changing the search condition of the established name of disease to hepatitis of a broader concept, there is a possibility that the number of target patients is increased more and the key does not correspond to the idiosyncratic information. Besides, by changing the search condition of the established name of disease to hepatic disease of a broader concept, there is a possibility that the number of target patients is increased even more and the key does not correspond to the idiosyncratic information.

This rounding setting screen may be designed to be automatically displayed on the terminal 14 of the user such as the researcher when there is the determination result of NG on the confirmation screen in FIG. 9, or it may also be designed to be displayed on the terminal 14 of the user such as the researcher when the researcher operates the terminal 14. Further, it is also possible to design such that the user such as the researcher can perform setting by using the terminal 14 or the manager can perform setting by using the medical information management system 10, through processing which is different from the anonymization processing illustrated in FIG. 4. In any of the above cases, in the present embodiment, the information set on the rounding setting screen is stored in the storage circuitry 22 of the medical information management system 10.

The researcher after finishing the confirmation on the confirmation screen in FIG. 9 transmits the confirmation result from the terminal 14 to the medical information management system 10. This confirmation result is received by the input circuitry 26 of the medical information management system 10 (step S8). Subsequently, when the confirmation result requests processing of anonymization, the anonymization processing execution function 20*d* in the processing circuitry 20 of the medical information management system 10 further performs anonymization processing on the condition-matched medical information after being subjected to the anonymization processing of deleting the personal information in step S3 in FIG. 4. Specifically, processing of deleting the value of the key determined as the idiosyncratic information from the condition-matched medical information or rounding the value of the key determined as the idiosyncratic information by setting the value to a value of a broader concept, is performed (step S9).

Next, the medical information management system 10 outputs the condition-matched medical information after being subjected to the anonymization processing (step S10). Concretely, the output circuitry 24 of the medical information management system 10 transmits the condition-matched medical information after being subjected to the anonymization processing to the terminal 14 of the researcher, which allows the researcher to use this condition-matched medical information for the purpose of research. Alternatively, the output circuitry 24 of the medical information management system 10 stores to save the condition-matched medical information after being subjected to the anonymization processing in the storage circuitry 22.

As described above, with the use of the medical information network system 1 according to the present embodiment, the medical information management system 10 performs the processing of supporting the anonymization of the condition-matched medical information by detecting the idiosyncratic information such as the idiosyncratic description from the condition-matched medical information which matches the search condition, which enables to lighten the burden imposed on the researcher and the like being the user. Further, it is possible to realize further stabilized anonymization by unifying a standard when performing the anonymization.

Further, since it is possible to set the essential key regarding which the purpose of utilization cannot be achieved if anonymization is performed, in the medical information management system 10, when the key including the value determined to include the idiosyncratic information such as the idiosyncratic description is the essential key, it is possible to call attention of the researcher and the like being the user. For this reason, it is possible to avoid the occurrence of problems such that the condition-matched medical information obtained by performing the anonymization processing cannot be utilized since it is insufficient in terms of the purpose of utilization for the researcher and the like.

Second Embodiment

In the above-described first embodiment, the processing of detecting the idiosyncratic information such as the idiosyncratic description is executed with respect to the condition-matched medical information which matches the search condition, but, the second embodiment is designed to execute the processing of detecting the idiosyncratic information such as the idiosyncratic description with respect to essential medical information obtained by deleting a key which is not essential and a value thereof from the condition-matched medical information which matches the search condition. Hereinafter, a part different from that of the above-described first embodiment will be explained.

Figure 11:
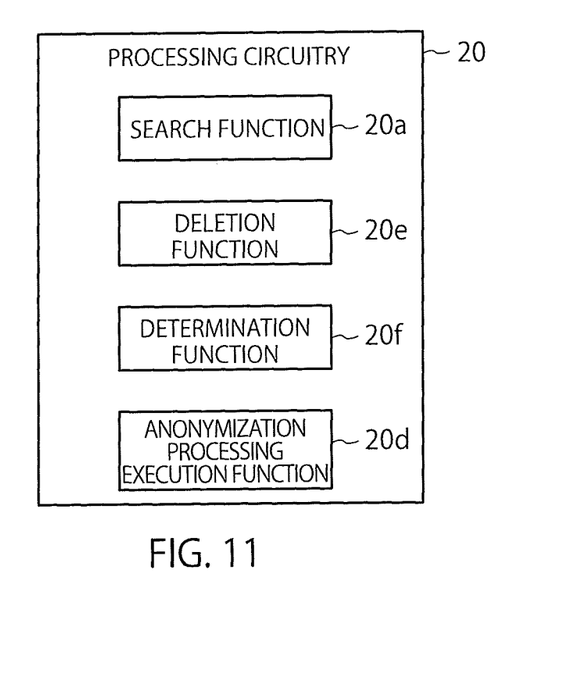
FIG. 11 is a diagram representing, by functional blocks, processing circuitry in a medical information management system according to a second embodiment.

FIG. 11 is a diagram representing, by functional blocks, processing circuitry 20 in a medical information management system 10 of a medical information network system 1 according to the second embodiment, and is a diagram corresponding to FIG. 3 in the above-described first embodiment. As illustrated in FIG. 11, the processing circuitry 20 according to the present embodiment configures a search function 20*a*, a deletion function 20*e*, a determination function 20*f*, and an anonymization processing execution function 20*d*. Concretely, the processing circuitry 20 reads and executes various kinds of programs stored in a storage circuitry 22, to thereby realize these search function 20*a*, deletion function 20e, determination function 20f, and anonymization processing execution function 20d. In the present embodiment, the search function 20a configures a searcher, the deletion function 20e configures a deleter, the determination function 20f configures a determiner, and the anonymization processing execution function 20d configures an anonymization processing executor. Further, a medical information management apparatus in the present embodiment is configured by the processing circuitry 20 including the search function 20a, the deletion function 20e, the determination function 20f, and the anonymization processing execution function 20d.

Figure 12:
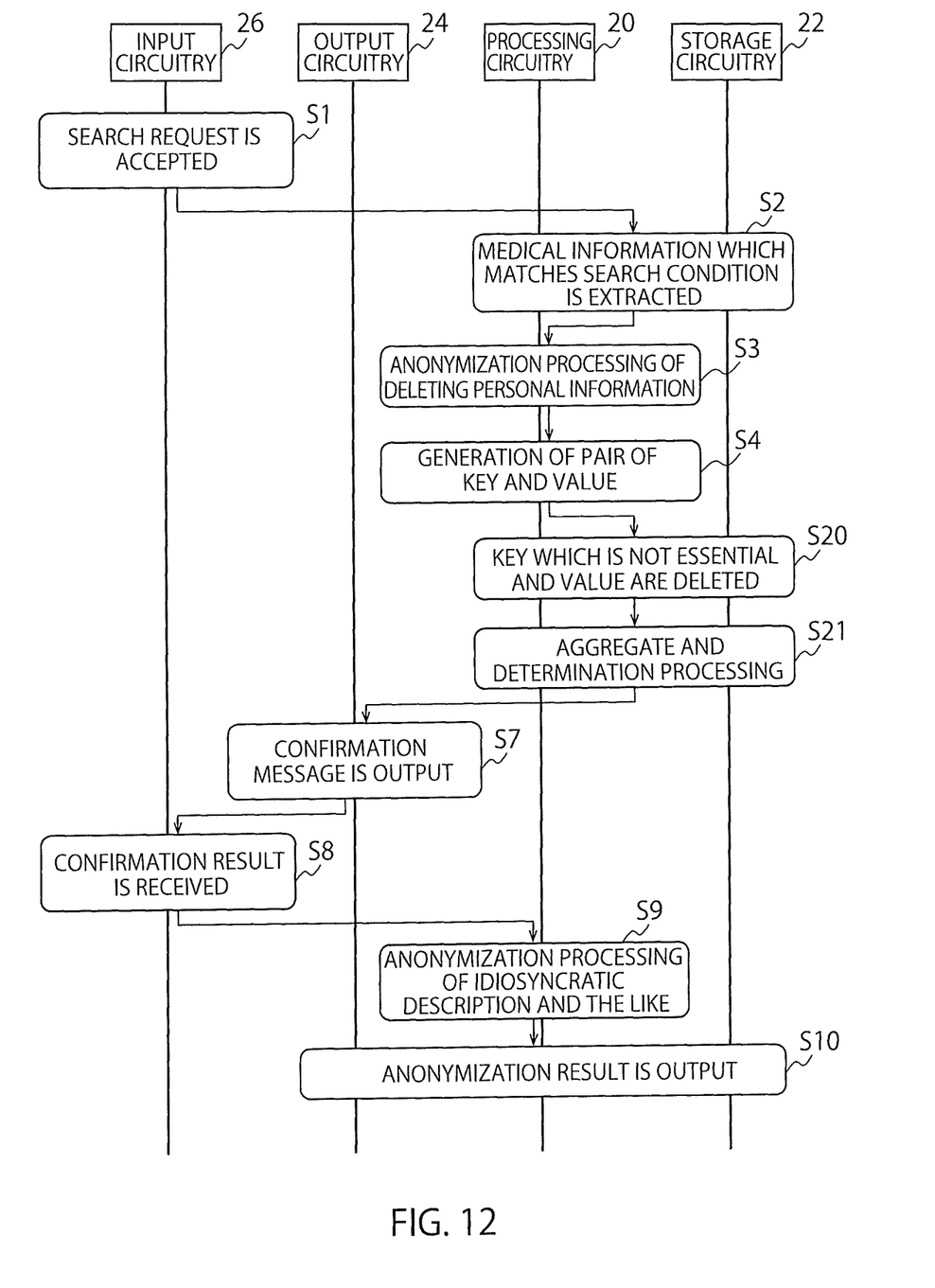
FIG. 12 is a diagram illustrating a processing flow which explains contents of anonymization processing executed by the medical information management system according to the second embodiment.

FIG. 12 is a diagram illustrating a processing flow which explains contents of anonymization processing executed by the medical information management system 10 according to the present embodiment, and is a diagram corresponding to FIG. 4 in the above-described first embodiment.

The anonymization processing according to the present embodiment illustrated in FIG. 12 is similar to the anonymization processing in the above-described first embodiment from step S1 to step S4. Further, after step S4, in the present embodiment, the deletion function 20e in the processing circuitry 20 of the medical information management system 10 classifies keys extracted in step S4 into a key which is essential in terms of the purpose of utilization and a key which is not essential in terms of the purpose of utilization, and then the key which is not essential and a value paired with the key which is not essential are deleted from the condition-matched medical information (step S20). The rest of medical information after the deletion becomes the essential medical information in the present embodiment.

For the discrimination between the key which is essential and the key which is not essential, for example, it is possible to use the essential key table as in FIG. 7 exemplified in the explanation of the above-described first embodiment. However, in the present embodiment, as a key which is essential, there is a necessity of setting a key as well which seems to be useful for the user such as the researcher in terms of the purpose of utilization, to a key which is essential. Specifically, information whose usefulness is recognized when it is utilized by the user for the purpose of research as medical information, becomes a key which is essential. On the contrary, a key whose usefulness is not recognized should be classified into a key which is not essential.

Next, as illustrated in FIG. 12, the determination function 20f in the processing circuitry 20 of the medical information management system 10 performs an aggregate with respect to the medical information stored in the storage circuitry 22, by using the key included in the essential medical information generated in step S20, and calculates a matching rate of the value included in the essential medical information (step S21). Namely, a matching rate being a proportion of each key included in the essential medical information generated in step S20 to the entire medical information stored in the storage circuitry 22 is calculated. For example, an aggregate is performed regarding the key of the established name of disease, and calculation regarding how much is a proportion occupied by lung cancer in the total number of cases of the medical information of patients storing the established names of diseases, is performed. Similarly, a matching rate of a value of another key included in the essential medical information is also calculated. Subsequently, when this matching rate is equal to or less than a predetermined threshold set for each key, the determination function 20f in the processing circuitry 20 determines that the value is idiosyncratic information being an idiosyncratic description and the like.

The relationship between the key and the threshold can be held by the threshold table as illustrated in FIG. 6 in the above-described first embodiment. Further, various modifications can be made such that for the threshold of the matching rate, a fixed value is set as the medical information management system 10 or an original fixed value is set in the medical information management system 10 for each hospital facility, without using the threshold table as in FIG. 6, and this point is similar to the above-described first embodiment.

Next, as illustrated in FIG. 12, the processing circuitry 20 of the medical information management system 10 outputs to transmit a confirmation message to the terminal 14 of the user such as the researcher via the output circuitry 24 (step S7). The processing of this step S7 and thereafter is similar to that of the above-described first embodiment.

As described above, with the use of the medical information network system 1 according to the present embodiment, it is designed to perform the determination regarding whether or not the idiosyncratic information such as the idiosyncratic description is included, with respect to the essential medical information obtained by deleting the key which is not essential and the value of the key from the condition-matched medical information, which enables to prevent even the medical information which is not required by the user such as the researcher from being provided.

Further, since it is designed to perform the processing of determining whether or not the idiosyncratic information such as the idiosyncratic description is included, on the essential medical information obtained by deleting the key which is not essential and the value of the key from the condition-matched medical information, it is possible to previously reduce the amount of information to be subjected to the determination.

While certain embodiments have been described above, these embodiments have been presented by way of example only, and are not intended to limit the scope of the inventions. Indeed, the novel apparatus and method described herein may be embodied in a variety of other forms; furthermore, various omissions, substitutions and changes in the form of the apparatus and the method described herein may be made without departing from the spirit of the inventions. The accompanying claims and their equivalents are intended to cover such forms or modifications as would fall within the scope and spirit of the inventions.

The invention claimed is:
1. A medical information management apparatus, comprising processing circuitry configured to:
    search medical information stored in a storage, when accepting a search request of the medical information from a user, and extract the medical information which matches a search condition as condition-matched medical information, wherein the medical information includes items of patient information and contents of the items and wherein the patient information includes a plurality of entry items;
    perform a process of specifying a plurality of entry items which correspond to idiosyncratic information from the plurality of entry items from which exclude a patient name and a patient identification, wherein the process includes:

extracting the items and the contents from the condition-matched medical information and perform first anonymization processing on the extracted items and contents, calculating a proportion of an amount of medical information in which the items, on which the anonymization processing is performed, are included compared to an entire amount of medical information stored in the storage, and determining that one of the contents is the idiosyncratic information when the proportion is equal to or less than a threshold, wherein the threshold is set with respect to each of the items, and there is a high possibility to specify a specific patient if the one of the contents is the idiosyncratic information;

determine whether or not the items of the contents including the idiosyncratic information corresponds to an essential key, wherein the essential key is a key which is essential in terms of a purpose of utilization of the condition-matched medical information;

generate and display a rounding setting screen on a terminal of the user if the idiosyncratic information corresponds to the essential key in terms of the purpose of the utilization, wherein the rounding setting screen causes the user to set the search condition to be a broader concept such that a number of target patients is increased; and receive a confirmation result from the user, and perform second anonymization processing on the condition-matched medical information on which the first anonymization processing was performed when the confirmation result requests processing to perform anonymization.

2. The medical information management apparatus according to claim 1, wherein the processing circuitry is further configured to:

perform the first anonymization processing by deleting personal information; and perform the second anonymization processing by deleting a value of a key determined to be idiosyncratic information.

3. The medical information management apparatus according to claim 1, wherein the processing circuitry is further configured to delete the value determined as the idiosyncratic information in the anonymization processing.

4. The medical information management apparatus according to claim 1, wherein the processing circuitry is further configured to set the value determined as the idiosyncratic information to a value of a broader concept in the second anonymization processing.

5. The medical information management apparatus according to claim 1, wherein:

the condition-matched medical information after being subjected to the second anonymization processing is transmitted to the user.

6. The medical information management apparatus according to claim 1, wherein:

the condition-matched medical information after being subjected to the second anonymization processing is output to the storage.

7. The medical information management apparatus according to claim 1, wherein the processing circuitry is further configured to cause the user to arbitrarily set a content of the essential key.

8. The medical information management apparatus according to claim 1, wherein the processing circuitry is further configured to output a confirmation message to a terminal of the user indicating whether the idiosyncratic information exists in the extracted medical information and whether the idiosyncratic information corresponds to the essential key.

9. A medical information management system, comprising:

a storage which stores medical information including a key being an item of information regarding a patient and a value being contents of the key; and processing circuitry configured to:

search the medical information stored in the storage, when accepting a search request of the medical information from a user, and extract the medical information which matches a search condition as condition-matched medical information, wherein the medical information includes items of patient information and contents of the items;

perform a process of specifying a plurality of entry items which correspond to idiosyncratic information from the plurality of entry items from which exclude a patient name and a patient identification, wherein the process includes:

extracting the items and the contents from the condition-matched medical information and perform first anonymization processing on the extracted items and contents;

calculating a proportion of an amount of medical information in which the items are included compared to an entire amount of medical information stored in the storage; and determining that one of the contents is idiosyncratic information when the proportion is equal to or less than a threshold, wherein the threshold is set with respect to each of the items, and there is a high possibility to specify a specific patient if the one of the contents is the idiosyncratic information to generate a first determination result;

determine whether or not the key of the value determined to include the idiosyncratic information corresponds to an essential key being a key which is essential in terms of a purpose of utilization to generate a second determination result;

output the condition-matched medical information, the first determination result, and the second determination result;

generate and display a rounding setting screen on a terminal of the user if the idiosyncratic information corresponds to the essential key in terms of the purpose of the utilization, wherein the rounding setting screen causes the user to set the search condition to be a broader concept such that a number of target patients is increased; and receive a confirmation result from the user, and perform second anonymization processing on the condition-matched medical information on which the first anonymization processing was performed when the confirmation result requests processing to perform anonymization.

10. The medical information management system according to claim 9, wherein:

the storage stores an essential key table holding the purpose of utilization and the essential key linked to the purpose of utilization; and the processing circuitry is further configured to obtain the essential key linked to the key from the essential key table stored in the storage to generate the second determination result.

11. The medical information management system according to claim 9, wherein:
the storage stores a threshold table holding the threshold set with respect to the key, and
the processing circuitry is further configured to obtain the threshold set with respect to the key from the threshold table stored in the storage to generate the first determination result.

12. The medical information management system according to claim 9, wherein the processing circuitry is configured to output the condition-matched medical information, the first determination result, and the second determination result to the user.

13. The medical information management system according to claim 9, wherein:
when the search request of the medical information is accepted from the user, the search request includes the purpose of utilization designated by the user; and
the processing circuitry is further configured to obtain the purpose of utilization in the search request to generate the second determination result.

14. The medical information management system according to claim 9, wherein:
when the search request of the medical information is accepted from the user, the search request includes the search condition designated by the user; and
the processing circuitry is further configured to extract the medical information which matches the search condition in the search request.

15. A medical information management apparatus, comprising processing circuitry configured to:
search medical information stored in a storage, when accepting a search request of the medical information from a user, and extract the medical information which matches a search condition as condition-matched medical information, wherein the medical information includes items of patient information and contents of the items;
classify the items included in the condition-matched medical information into an item which is essential and an item which is not essential in terms of a purpose of utilization, and delete the item which is not essential and a value corresponding to the item which is not essential from the condition-matched medical information to generate essential medical information;
perform a process of specifying entry items which correspond to idiosyncratic information from a plurality of entry items from which exclude a patient name and a patient identification, wherein the process includes:
extracting the items and the contents from the essential medical information, and perform first anonymization processing on the extracted items and contents,
calculating a proportion of an amount of medical information in which the items are included compared to an entire amount of medical information stored in the storage, and
determining that one of the contents is idiosyncratic information when the proportion is equal to or less than a threshold, wherein the threshold is set with respect to each of the items, and there is a high possibility to specify a specific patient if the one of the contents is the idiosyncratic information;
generate and display a rounding setting screen on a terminal of the user if the idiosyncratic information corresponds to an essential key in terms of the purpose of the utilization, wherein the rounding setting screen causes the user to set the search condition to be a broader concept; and
receive a confirmation result from the user, and perform second anonymization processing on the condition-matched medical information on which the first anonymization processing was performed when the confirmation result requests processing to perform anonymization.

16. The medical information management apparatus according to claim 15, wherein the processing circuitry is further configured to:
perform the first anonymization processing by deleting personal information; and
perform the second anonymization processing by deleting a value of a key determined to be idiosyncratic information.

17. The medical information management apparatus according to claim 15, wherein the processing circuitry is further configured to delete the value determined as the idiosyncratic information in the anonymization processing.

18. The medical information management apparatus according to claim 15, wherein the processing circuitry is further configured to set the value determined as the idiosyncratic information to a value of a broader concept in the anonymization processing.

19. The medical information management apparatus according to claim 15, wherein:
the essential medical information after being subjected to the anonymization processing is transmitted to the user.

20. The medical information management apparatus according to claim 15, wherein:
the essential medical information after being subjected to the anonymization processing is output to the storage.

* * * * *